United States Patent
Al-Jabr et al.

(10) Patent No.: US 9,596,851 B1
(45) Date of Patent: Mar. 21, 2017

(54) METHOD FOR CONTROLLING GROWTH OF RED PALM WEEVIL

(71) Applicant: KING FAISAL UNIVERSITY, Al-Ahsa (SA)

(72) Inventors: Ahmed Mohammed S. Al-Jabr, Al-Ahsa (SA); Abid Hussain, Al-Ahsa (SA); Muhammad Rizwan-Ul-Haq, Al-Ahsa (SA); Hassan Al-Ayedh, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 14/975,422

(22) Filed: Dec. 18, 2015

(51) Int. Cl.
*A01N 61/00* (2006.01)
*A01N 43/16* (2006.01)
*A01N 25/02* (2006.01)

(52) U.S. Cl.
CPC ............. *A01N 43/16* (2013.01); *A01N 25/02* (2013.01); *A01N 61/00* (2013.01)

(58) Field of Classification Search
None
See application file for complete search history.

(56) References Cited

U.S. PATENT DOCUMENTS

| | | | |
|---|---|---|---|
| 4,003,964 A * | 1/1977 | Oswald | A01N 57/10 558/162 |
| 2005/0049230 A1 | 3/2005 | Henrich et al. | |
| 2012/0329832 A1 | 12/2012 | Delaveau et al. | |

OTHER PUBLICATIONS

Moreira et al. "Plant compounds Insecticide Activity Against Coleopetera Pests of Stored Products," Agropec. Bras. Brasilia, 2007, vol. 42, No. 7, pp. 909-915.*
Web Page Red Palm Weevil: web address: cisr.ucr.edu/red_palm_weevil.html, accessed May 20, 2016.*

\* cited by examiner

*Primary Examiner* — Kortney L Klinkel
*Assistant Examiner* — William Lee
(74) *Attorney, Agent, or Firm* — Richard C. Litman

(57) ABSTRACT

A method for controlling growth of Red Palm Weevil includes administering to the Red Palm Weevil a composition including a pesticidally effective amount of coumarin and an agriculturally-acceptable carrier.

6 Claims, 3 Drawing Sheets

METHOD FOR CONTROLLING GROWTH OF RED PALM WEEVIL

BACKGROUND OF THE INVENTION

1. Field of the Invention

The present invention relates to pesticides, and particularly to use of a phenylpropanoid plant secondary metabolite for controlling Red Palm Weevil infestations.

2. Description of the Related Art

Red Palm Weevil (RPW), *Rhynchophorus ferrugineus* (Coleoptera, Curculionidae), is the most damaging tissue boring pest of palms or palm trees. It likely originated from India and subsequently spread worldwide due to the poor quarantine measures. Infestations of this pest have been reported on more than 28 palm species worldwide. The coconut palm, the canary palm, and the date palm, in particular, have suffered significantly from the damaging effects of the Red Palm Weevil. Legless creamy white larvae (so-called "grubs") of Red Palm Weevil are the most destructive stage of the weevil. They chew the soft tender tissues and move towards the interior of the palm. Weevil larvae can excavate holes in the trunk of palm trees up to a meter long, thereby weakening and eventually killing the host plant. The recent statistics shows that red palm weevil infestation may cause severe economic losses that account for about 5.18 to 25.92 million USD annually.

The life cycle of Red Palm Weevil is comprised of 3-4 months depending upon the environmental conditions. Female Red Palm Weevil singly lays eggs into the holes made by Rhinoceros beetles or wounds made during pruning. Hatched creamy white larvae (grubs) start feeding on surrounding tissues and complete their sixteen instars. Such feeding pattern destroys the vascular system of the palm trees resulting in death of the infested palm within one year.

Currently, Red Palm Weevil infestations are controlled by frequent application of synthetic pesticides as soil treatment, tree fumigation, trunk injection, wound dressing and crown drenching of infested palms. These practices are not sustainable, endanger biological diversity and deteriorate environmental quality.

Thus, use of a bio-pesticide to control infestations of Red Palm Weevil solving the aforementioned problems is desired.

SUMMARY OF THE INVENTION

A method for controlling Red Palm Weevil, such as by eliminating or deterring the growth of a Red Palm Weevil population, can include using a composition including a pesticidally effective amount of coumarin and an agriculturally-acceptable carrier. The method includes the step of administering to the Red Palm Weevil a pesticidally effective amount of the composition. The concentration of coumarin in the composition can be in a range from about 200 mg/L to about 1000 mg/L or from about 200 to about 1000 ppm. The composition may include a larval food composition and may be applied by spraying the composition on a Red Palm Weevil host, e.g., a palm tree.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
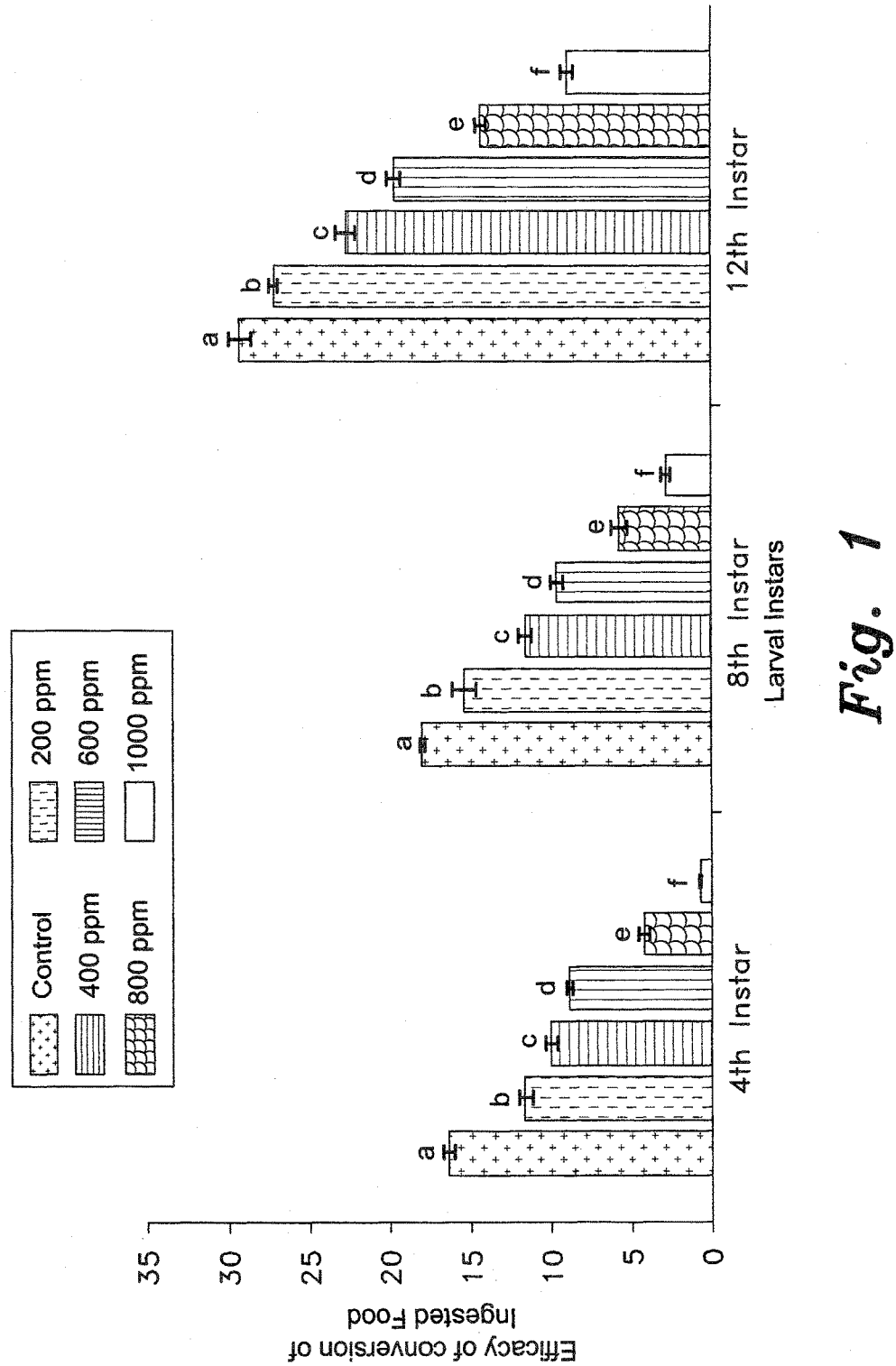
FIG. 1 shows the efficacy of conversion of ingested food by different larval instars ($4^{th}$, $8^{th}$ and $12^{th}$ instar) fed different concentrations of coumarin.

A method for controlling Red Palm Weevil, such as by eliminating or deterring the growth of a Red Palm Weevil population, can include using a composition including a pesticidally effective amount of coumarin and an agriculturally-acceptable carrier. The method includes the step of administering to the Red Palm Weevil a pesticidally effective amount of the composition. Controlling growth of Red Palm Weevil includes damage to the Red Palm Weevil, inhibition or modulation of Red Palm Weevil growth, inhibition of Red Palm Weevil reproduction by slowing or arresting its proliferation, or complete destruction/death of the Red Palm Weevil.

Coumarin is phenylpropanoid plant secondary metabolite synthesized by phenylalanine within the plants by the shikimic acid pathway. The compound was initially discovered from Dipteryx odorata Wild. Currently, over 1300 coumarins have been identified from greater than 150 plant species. The insecticidal potential of coumarin has been explored against numerous insect pests including *Oryzaephilus surinamensis, Rhyzopertha dominica, Sitophilus zeamais, Spodoptera frugiperda, Spodoptera littoralis* and mosquitoes.

The composition can include coumarin and an agriculturally acceptable carrier. The agriculturally acceptable carrier can include a water solvent and/or an organic solvent, such as acetone, ether, ketone, kerosene, or alcohol, in a concentration of organic solvent that will not harm a host tissue if applied to a host tissue. The concentration of coumarin in the composition can be in a range from about 200 mg/L to about 1000 mg/L or from about 200 ppm to about 1000 ppm.

Administering the composition to the Red Palm Weevil can include application of the composition to a Red Palm Weevil host. For example, the composition can be applied to a palm tree. The composition can deter, incapacitate, and/or kill Red Palm Weevil that feed on palm plant tissue. The composition can protect palms from Red Palm Weevil at any stage of development. The composition can protect the palms from Red Palm Weevil larvae. The composition can include a larval food composition. The composition can be applied to the Red Palm Weevil or a site of Red Palm Weevil infestation. The composition can be administered in any suitable manner, e.g., by spraying the composition on a palm surface. Other application methods can include ground, aerial, surface, soil incorporation, brushing, dipping, and the like.

The present composition provides efficacious pesticides which can be designated as biorational. A biorational pesticide is a chemical substance of natural origin that can be synthesized. The present composition can have a lethal effect on Red Palm Weevil targets. Unlike the bulk of currently available pesticides on the market, the present compositions are substantially non-toxic to man and domestic animals and have minimal adverse effects on wildlife and the environment.

The term "pesticidally effective amount" is an amount of the compound, or a composition containing the compound, that has an adverse affect on at least 25% of the pests treated, more preferably at least 50%, most preferably at least 70% or greater. The $EC_{50}$ is the concentration of a drug that gives half-maximal response. The $LD_{50}$ is a standard measurement of acute toxicity that is stated in milligrams (mg) of pesticide per kilogram (kg) of body weight. An $LD_{50}$ represents the individual dose required to kill 50 percent of a population of the subject insects or pests.

The efficacy of the composition was monitored by determining the mortality of or damage to the Red Palm Weevil population. $LD_{50}$ and $EC_{50}$ values of 4th instar larvae determined after three days of experimentation were 404.55 ppm and 293.77 ppm, respectively as shown in Table 1. Relatively higher doses were calculated for higher instars. For instance, the 8th instar larvae showed 438.32 ppm ($EC_{50}$) and 509.37 ppm ($LD_{50}$), while the 12th instar larvae showed 559.77 ppm ($EC_{50}$) and 708.24 ppm ($LD_{50}$).

The composition offers several advantages over currently used pesticides. First, coumarin is a naturally-occurring compound, and as such is expected to generally exhibit a very high $LD_{50}$ against animals and thus are relatively nontoxic to humans, domestic animals and wildlife. By using the composition, the environmental and health hazards involved in pest control are minimized by reducing the toxicity of the chemical compounds. Because of the low toxicity, when necessary, the composition can be used as a preventative on a repeated basis and, thus, can be integrated into integrated pest management (IPM) programs. The composition may be solid (i.e., in a powdered form) or liquid depending on the carrier and the needs of the user. If the composition is solid, suitable carriers include various known, agriculturally-useful powders that are generally used for this purpose. If the composition is liquid, it may be aqueous or non-aqueous and may be a solution, suspension, or emulsion, depending on the needs of the user applying the pesticidal composition.

The composition can include an antioxidant at a level sufficient to increase the product shelf life. Suitable antioxidants, include, but are not limited to, ascorbyl palmitate, anoxomer, benzoic acid, benzlkonium chloride, benzethonium chloride, benzyl alcohol, butylated hydroxyanisole, butylated hydroxytoluene, chlorobutanol, dehydroacetic acid, ethylenediamine, ferulic acid, potassium benzoate, potassium metabisulfite, potassium sorbate, n-propyl gallate BP, propylparaben, sassafras oil, sodium benzoate, sodium bisulfite, sodium metabisulfite, sorbic acid, vitamin E, eugenol, .alpha.-tocopherol, and the like. Particularly suitable antioxidants include sodium benzoate, vitamin E and .alpha.-tocopherol. Antioxidants can be included in the composition so long as the formulation remains biologically compatible if applied to a host.

For controlling the growth of pests on a plant or a plant part (such as foliage/leaves, trunk, stems, branches or roots and so forth), the method can be carried out by applying a pesticidally effective amount of the composition to a palm host in which the Red Palm Weevil is growing or is to be grown. The method of introduction of the composition into the target pest can be by contacting the pest, by direct ingestion by the target pest from a trap, or by feeding a target pest on nutrient-providing, organic matter treated with the pesticide. In some instances, the pesticide is absorbed by the pest, particularly where the formulation provides for uptake by the outer tissues of the pest, particularly a larval or other pre-adult form of the pest. For some applications, it may be necessary to deliver the formulation to the location of the pest colony. For example, the composition can be sprayed on as a wet or dry composition on the palm surface infested with a target pest, or surface susceptible to infestation with a target pest. Alternately, the composition can be applied wet or dry to an area of infestation where it can contact the target pest.

The following examples will further illustrate the insecticidal potential of coumarin as a bio-pesticide on the growth and development of different larval instars of red palm weevil.

Example 1

Insecticidal Potential of Coumarin at Different Doses

Insecticidal potential of coumarin at different dose concentrations (200 ppm, 400 ppm, 600 ppm, 800 ppm and 1000 ppm) was evaluated against $4^{th}$, $8^{th}$ and $12^{th}$ instar Red Palm Weevil larvae. The above mentioned concentrations of coumarin were prepared by dissolving coumarin in 0.05% acetone. The ingredients of artificial diet (wheat flour @ 45 g/L, corn flour @ 45 g/L, Yeast @ 45 g/L, Agar @ 17.5 g/L, Sorbic acid @ 1.6 g/L, L-Ascorbic Acid @ 4 g/L, Pharmaton (2 capsules/L), Tetracycline @ 500 mg/L) were dissolved in 1 L of coumarin solution with strength 200 mg/L, 400 mg/L, 600 mg/L, 800 mg/L and 1000 mg/L, separately. The newly moulted $4^{th}$, $8^{th}$ and $12^{th}$ instar Red Palm Weevil larvae were allowed to feed on each diet separately in perforated plastic bowls. In case of control treatment, 0.05% acetone was used to prepare the diet. Twenty larvae were used to compile one replicate. Five replicates were prepared likewise. The fresh diet was provided daily to the larvae. The experimental units were incubated at 30±1° C. and 75%±5% relative humidity. Abbot formula was used to correct the control mortality (Abbott, 1925). Efficacy of coumarin was determined at each dose to calculate $LD_{50}$ values. Results showed that the dose of coumarin is directly proportional to the mortality of the $4^{th}$, $8^{th}$ and $12^{th}$ instar Red Palm Weevil larvae. $LD_{50}$ and $EC_{50}$ values of $4^{th}$ instar larvae determined after three days of experimentation were 404.55 ppm and 293.77 ppm, respectively as shown in Table 1. Relatively higher doses were calculated for higher instars. For instance, the $8^{th}$ instar larvae showed 438.32 ppm ($EC_{50}$) and 509.37 ppm ($LD_{50}$), while the $12^{th}$ instar larvae showed 559.77 ppm ($EC_{50}$) and 708.24 ppm ($LD_{50}$).

TABLE 1

Effective concentrations (ppm) of coumarin against different larval instars of Red Palm Weevil

| Larval Instar | $EC_{50}$ | Slope ± SE | $LD_{50}$ | Slope ± SE |
|---|---|---|---|---|
| $4^{th}$ instar | 293.77 ppm | 2.76 ± 0.27 | 404.55 ppm | 3.13 ± 0.27 |
| $8^{th}$ instar | 438.32 ppm | 2.86 ± 0.27 | 509.37 ppm | 2.96 ± 0.28 |
| $12^{th}$ instar | 559.77 ppm | 2.93 ± 0.28 | 708.24 ppm | 2.89 ± 0.30 |

Example 2

Impact of Different Doses of Coumarin on the Growth and Development of Different Larval Instars of Red Palm Weevil Impact of different doses of coumarin on the growth and development of different larval instars of red palm weevil was evaluated by growth indices bioassays. All the solutions of coumarin were prepared by dissolving in 0.05% acetone. The ingredients of artificial diet (wheat flour @ 45 g/L, corn flour @ 45 g/L, Yeast @ 45 g/L, Agar @ 17.5 g/L, Sorbic acid @ 1.6 g/L, L-Ascorbic Acid @ 4 g/L, Pharmaton (2 capsules/L), Tetracycline @ 500 mg/L) were dissolved in 1 L of coumarin solution with strength 200 mg/L, 400 mg/L, 600 mg/L, 800 mg/L and 1000 mg/L of coumarin, separately. Newly moulted $4^{th}$, $8^{th}$ and $12^{th}$ instar Red Palm Weevil larvae were allowed to feed on each diet separately in perforated plastic bowls. In case of control treatment, 0.05% acetone was used to prepare the diet. Twenty larvae were used to compile one replicate. Five replicates were prepared likewise. The fresh diet was daily provided to the larvae. The experimental units were incubated at 30±1° C. and 75%±5% relative humidity. Initial and final weight of the larvae and the frass produced during 72 hours post exposure was also measured. These measurements were used to determine the impact of coumarin on the nutritional indices including: Approximate Digestibility [AD=(food digested−frass weight)/food ingested×100], Efficacy of conversion of digested food [ECD=weight gained by the larva/(food ingested−dry weight of frass)×100] and Efficacy of conversion of ingested food [ECI=100×dry weight gained by the larva/dry weight of food consumed].

For growth indices, measurements were made 72 hours post-exposure on dry matter basis. Larvae, frass and remaining food after 72 h were dried at 60° C. until constant weight. Growth indices data were analyzed by one way analysis of variance (ANOVA). Means were compared by Fisher's Least Significant Difference (LSD) test.

Figure 2:
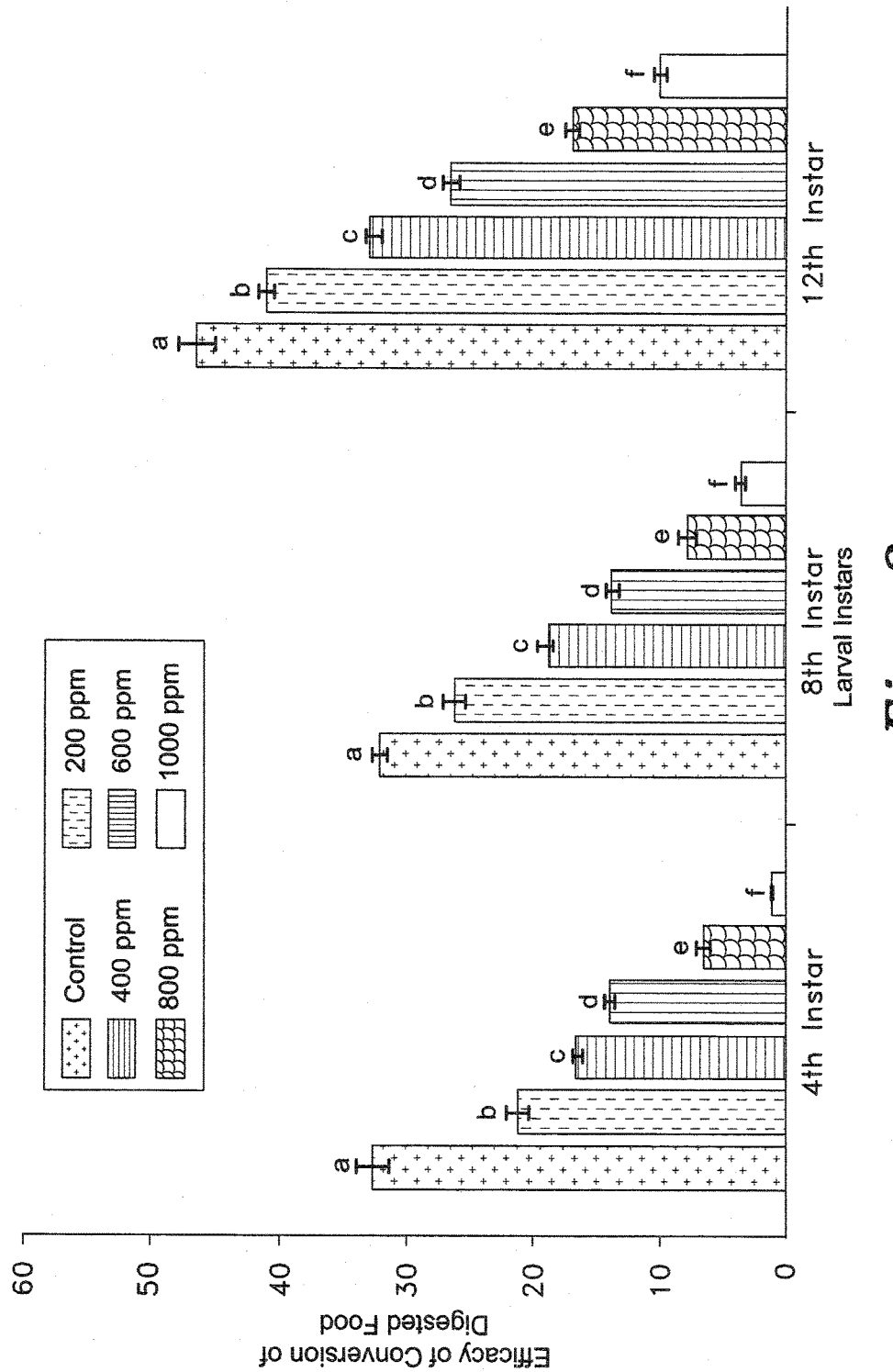
FIG. 2 shows the efficacy of conversion of digested food by different larval instars (4th, 8th and 12th instar) fed different concentrations of coumarin.
Figure 3:
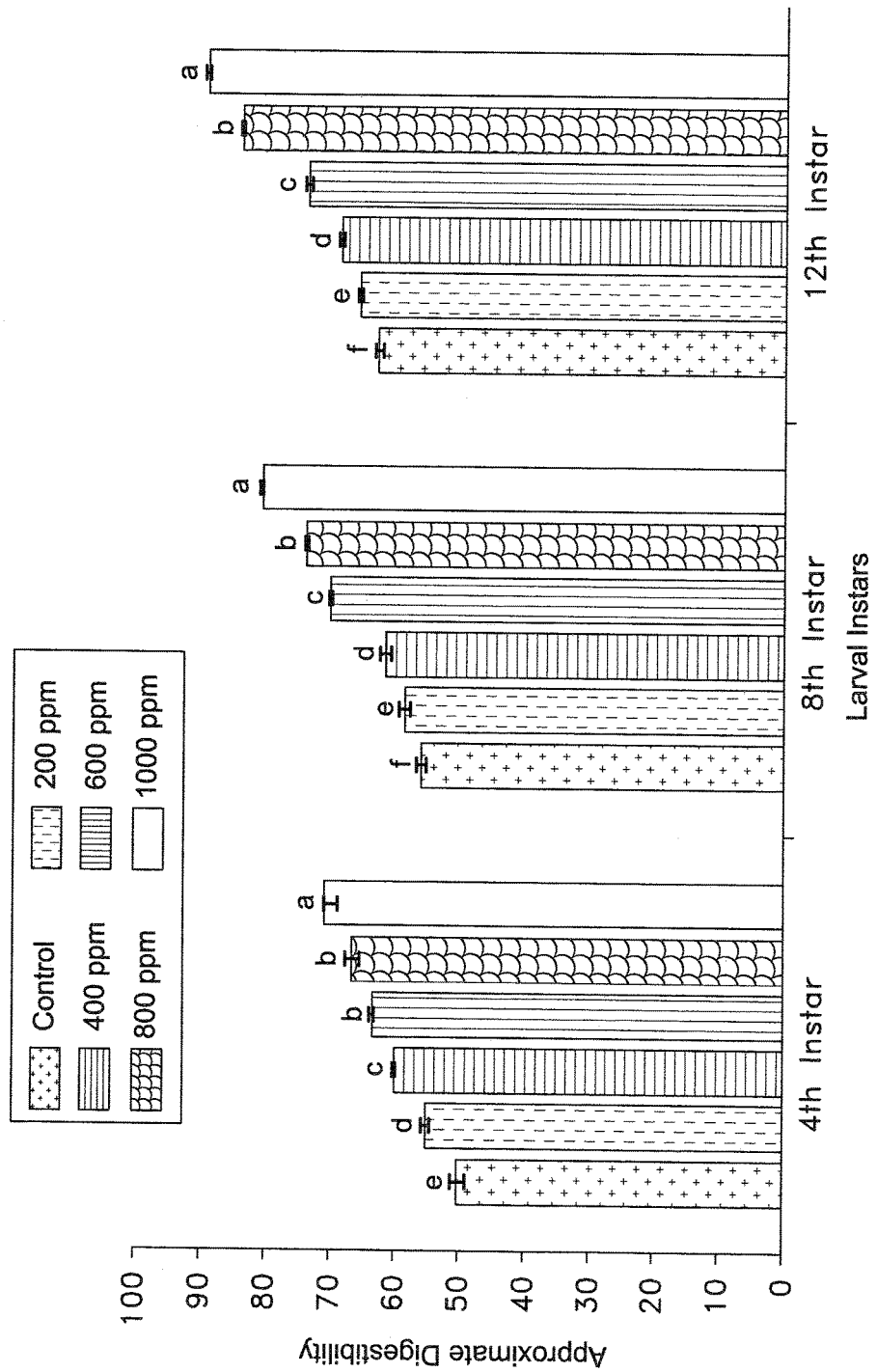
FIG. 3 shows the approximate digestibility of different larval instars (4th, 8th and 12th instar) fed different concentrations of coumarin.

The efficacy of the conversion of ingested food upon exposure with different concentrations differed significantly among $4^{th}$ (F=261.75; df=4, 20; P<0.0001), $8^{th}$ (F=410.30; df=4, 20; P<0.0001) and $12^{th}$ instar (F=592.91; df=4, 20; P<0.0001) larvae. Artificial diet incorporated with highest dose 1000 ppm of coumarin greatly reduced the ECI resulting in 95.59%, 84.03% and 69.43% inhibition compared to control among $4^{th}$, $8^{th}$ and $12^{th}$ instar larvae as illustrated in FIG. 1. Meanwhile, the inventors have also observed significant differences in the efficacy of the conversion of digested food upon exposure with different concentrations among $4^{th}$ (F=223.96; df=4, 20; P<0.0001), $8^{th}$ (F=426.41; df 4, 20; P<0.0001) and $12^{th}$ instar (F=494.23; df=4, 20; P<0.0001) larvae. Artificial diet incorporated with highest dose (1000 ppm) tremendously reduced ECD resulting in 96.88%, 88.99% and 78.52% inhibition compared to control among $4^{th}$, $8^{th}$ and $12^{th}$ instar larvae as illustrated in FIG. 2. The approximate digestibility (AD), however, significantly increased upon exposure with different isolates against all studied instars including $4^{th}$ (F=45.44; df=4, 20; P<0.0001), $8^{th}$ (F=291.67; df=4, 20; P<0.0001) and $12^{th}$ instar (F=879.84; df=4, 20; P<0.0001) larvae as illustrated in FIG. 3. In FIGS. 1-3, numerical values are the mean values of five replicates (n=20). Mean±SE values within a column followed by different letter(s) are significantly different. (Fisher's Least Significant Difference (LSD) test, P<0.05).

It is to be understood that the present invention is not limited to the embodiments described above, but encompasses any and all embodiments within the scope of the following claims.

We claim:

1. A method for controlling growth of Red Palm Weevil, wherein the Red Palm Weevil includes Red Palm Weevil instar larvae, comprising administering to the Red Palm Weevil an effective amount of a composition comprising an agriculturally-acceptable carrier and coumarin, wherein the concentration of coumarin in the composition is in a range of from about 200 mg/L to about 1000 mg/L.

2. The method for controlling growth of Red Palm Weevil according to claim 1, wherein the agriculturally acceptable carrier is water or an organic solvent.

3. The method for controlling growth of Red Palm Weevil according to claim 1, wherein the agriculturally acceptable carrier is acetone.

4. The method for controlling growth of Red Palm Weevil according to claim 1, wherein the composition is administered by contacting a Red Palm Weevil host with the composition.

5. The method for controlling growth of Red Palm Weevil according to claim 1, wherein the Red Palm Weevil host is a palm tree.

6. A method for preventing Red Palm Weevil infestation of a palm tree, comprising:
contacting the palm tree with an effective amount of a composition including an agriculturally-acceptable carrier and coumarin, wherein the concentration of coumarin in the composition is in a range of from about 200 mg/L to about 1000 mg/L.

* * * * *